(12) United States Patent
Bowman

(10) Patent No.: US 7,753,854 B2
(45) Date of Patent: *Jul. 13, 2010

(54) BLOOD FLOW MONITOR WITH ARTERIAL AND VENOUS SENSORS

(75) Inventor: Harry Frederick Bowman, Needham, MA (US)

(73) Assignee: Thermal Technologies, Inc, Cambrige, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/380,623

(22) Filed: Mar. 2, 2009

(65) Prior Publication Data

US 2009/0216136 A1    Aug. 27, 2009

Related U.S. Application Data

(60) Continuation of application No. 10/809,120, filed on Mar. 24, 2004, now Pat. No. 7,527,598, which is a continuation-in-part of application No. 10/364,773, filed on Feb. 11, 2003, now Pat. No. 6,913,576, which is a continuation of application No. 09/733,595, filed on Dec. 8, 2000, now Pat. No. 6,565,516, which is a division of application No. 08/946,366, filed on Oct. 7, 1997, now Pat. No. 6,203,501, which is a division of application No. 08/106,068, filed on Aug. 13, 1993, now Pat. No. 5,797,398.

(60) Provisional application No. 60/458,100, filed on Mar. 26, 2003.

(51) Int. Cl.
*A61B 5/00* (2006.01)

(52) U.S. Cl. .................................. 600/505; 600/526

(58) Field of Classification Search .................. None
See application file for complete search history.

(56) References Cited

U.S. PATENT DOCUMENTS

| | | | | | |
|---|---|---|---|---|---|
| 4,217,910 | A | * | 8/1980 | Khalil | 600/483 |
| 5,009,234 | A | * | 4/1991 | Alt | 600/485 |
| 5,692,514 | A | * | 12/1997 | Bowman | 600/504 |
| 5,797,398 | A | * | 8/1998 | Bowman | 600/505 |
| 7,527,598 | B2 | * | 5/2009 | Bowman | 600/505 |

* cited by examiner

*Primary Examiner*—Robert L Nasser
(74) *Attorney, Agent, or Firm*—James L. Neal

(57) ABSTRACT

A technique is disclosed for determining blood flow in a living body by changing the thermal energy level in the venous blood flow path and determining temperatures in both the venous and arterial blood flow paths. Blood flow is calculated as a function of the change in energy level and the temperature differences in the venous and arterial blood flow paths.

7 Claims, 7 Drawing Sheets

PROCESS I

PROCESS III

PROCESS IV

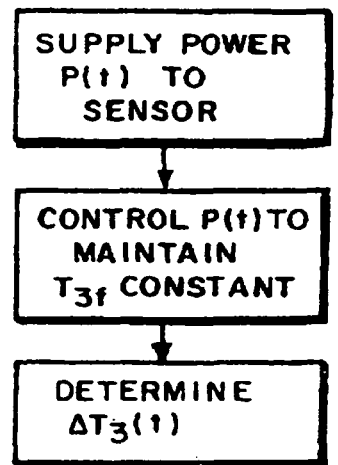
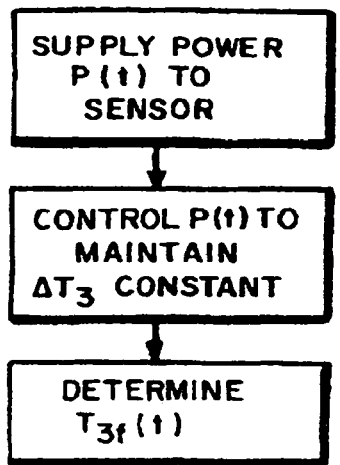
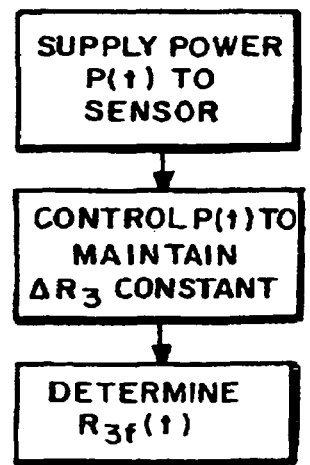
FIG.8A  FIG.8B  FIG.8C
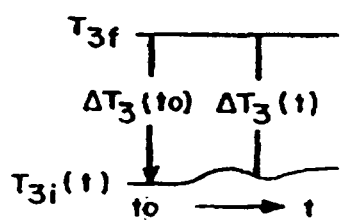
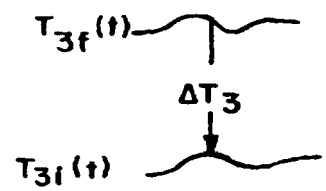
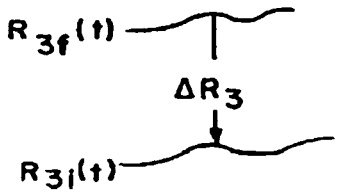
FIG.9A  FIG.9B  FIG.9C
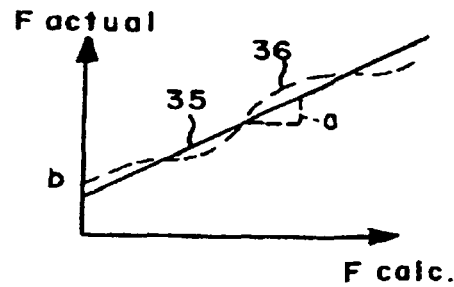
FIG.10

BLOOD FLOW MONITOR WITH ARTERIAL AND VENOUS SENSORS

This application is a continuation of U.S. application Ser. No. 10/809,120, filed Mar. 24, 2004, now U.S. Pat. No. 7,527, 598, which is a continuation-in-part of U.S. application Ser. No. 10/364,773, filed Feb. 11, 2003, now U.S. Pat. No. 6,913, 576, which is a continuation of U.S. application Ser. No. 09/733,595, filed Dec. 8, 2000, now U.S. Pat. No. 6,565,516, which is a divisional of U.S. application Ser. No. 08/946,366, filed Oct. 7, 1997, now U.S. Pat. No. 6,203,501, which is a divisional of U.S. application Ser. No. 08/106,068, filed Aug. 13, 1993, now U.S. Pat. No. 5,797,398. In addition, Ser. No. 10/809,120 claims benefit to provisional application 60/458, 100, filed Mar. 26, 2003.

INTRODUCTION

This invention relates generally to techniques for measuring blood flow in a body and, more particularly, to the use preferably of one or more temperature sensors for measuring thermal energy changes in the blood flowing through the heart and to the use of unique data processing techniques in response thereto for determining cardiac output.

BACKGROUND OF THE INVENTION

While the invention can be used generally to measure blood flow at various locations in a body, it is particularly useful in measuring blood flow in the heart so as to permit the measurement of cardiac output. Many techniques for measuring cardiac output have been suggested in the art. Exemplary thermodilution techniques described in the technical and patent literature include: "A Continuous Cardiac Output Computer Based On Thermodilution Principles", Normann et al., Annals of Biomedical Engineering, Vol. 17, 1989; "Thermodilution Cardiac Output Determination With A single Flow-Directed Catheter", Forrester, et al., American Heart Journal, Vol. 83, No. 3, 1972; "Understanding Techniques for Measuring Cardiac Output", Taylor, et al., Biomedical Instrumentation & Technology, May/June 1990; U.S. Pat. No. 4,507,974 of M. L. Yelderman, issued Apr. 2, 1985; U.S. Pat. No. 4,785,823, of Eggers et al., issued on Nov. 22, 1988; and U.S. Pat. No. 5,000,190, of John H. Petre, issued on Mar. 19, 1991.

A principal limitation in the quantification of cardiac output is the existence of thermal fluctuations inherent in the bloodstream. Previous methods work with those fluctuations while observing the effects of an input signal to calculate cardiac output. The invention described herein uses a differential measurement technique to substantially eliminate the effect of the thermal fluctuations, permitting the use of a minimal thermal input signal, which allows frequent or continuous measurements.

It is desirable to obtain accurate cardiac output measurements in an effectively continuous manner, i.e., several times a minute, so that a diagnosis can be achieved more rapidly and so that rapid changes in a patient's condition can be monitored on a more continuous basis than is possible using current techniques. Moreover, it is desirable to obtain instantaneous measurements of the cardiac output on a beat-to-beat basis to evaluate the relative changes which occur from beat to beat, as well as to determine the presence of regurgitation.

BRIEF SUMMARY OF THE INVENTION

In accordance with general principal of the invention, blood flow and/or cardiac output is determined rapidly, using a technique by which an indicator substance, or agent, is introduced into the bloodstream between a pair of detectors. The detectors are sensitive to a parameter functionally related to the concentration or magnitude in the bloodstream of the selected indicator agent. The detectors are positioned apart by a distance functionally sufficient to allow a measurement to be made of the differential value of the selected parameter as it exists from time-to-time between the two detectors. The indicator agent, for example, may be a substance to change the pH of the blood, a fluid bolus carrying thermal energy, or a substance to change a selected characteristic of the blood, or the direct introduction of thermal energy, or the like.

A determination is made of the difference in the values of the selected blood parameter as it exists at the two detectors, prior to the introduction of indicator agent (i.e., the first differential value). The selected indicator agent is then introduced in a predetermined magnitude. Then again a determination is made of the difference in values of the selected parameter as it exists at the locations of the two detectors (i.e., the second differential value).

Blood flow or cardiac output, depending on the specific location of the detectors, can then be determined as a function of the difference between the first differential value and the second differential value. Because the ultimate measurement of blood flow or cardiac output is based on the difference of the differences, the system operates effectively with the introduction of the indicator agent in a very low magnitude. In turn, this allows measurements to be made rapidly so that effectively continuous measurements are obtained.

In accordance with a preferred embodiment of the invention, for example, cardiac output can be determined rapidly and with low levels of thermal energy input. To achieve such operation, in a preferred embodiment, the technique of the invention uses a pair of temperature sensors positioned at two selected locations within a catheter which has been inserted into the path of the blood flowing through the heart of a living body. The, sensors detect the temperature difference between the two locations. Depending on the location of the temperature sensors in the circulatory system, the measured temperature difference varies over time. It has been observed that when the temperature sensors are placed within the heart, e.g., so that one sensor lies in the vena cava, for example, and the second in the right ventricle or pulmonary artery, the temperature difference varies in a synchronous manner with the respiratory cycle.

Thus, in the preferred embodiment of the invention the temperature difference over at least one respiratory cycle is measured and averaged to provide an average temperature difference. The averaging, or integrating, action effectively eliminates, as a confounding factor in the determination of cardiac output, the effect of instantaneous blood temperature fluctuations, such as cyclical, respiratory-induced fluctuations.

To make such determinations, an average temperature difference is first calculated over a time period of at least one respiratory cycle in which no thermal energy is introduced into the blood flow path. Thermal energy of a predetermined and relatively low magnitude is then introduced into the blood flow path to produce a heating action therein at a location between the two temperature sensors. Once the temperature rise induced by the heating stabilizes, the average temperature difference between the two locations is again calculated from temperature difference measurements over a time period of at least one respiratory cycle at the higher temperature level. The difference between the average temperature differences which occurs when the thermal energy is turned on, referred to as the rising temperature change, is determined. The difference between the average temperature differences which occurs when the thermal energy is turned off, referred to as the falling temperature change, is similarly determined. The cardiac output is calculated as a function of the thermal energy input and the rising and falling temperature changes. Because a relatively low level of thermal energy is used in making measurements, the overall sequence of determinations can be safely repeated multiple times per minute, for example, so that an effectively continuous, or quasi-continuous, determination of cardiac output is obtained.

Further, a pair of sensors may be introduced into the circulatory system at other locations in a subject. For example, a catheter may be introduced into the venous side of the circulatory system to locate an energy source (e.g.: a heater) in or near the vena cava or within the heart. A sensor may be located in the venous side of the circulatory system, upstream of the energy source, anywhere that temperature is not materially affected by output from the energy source. This sensor is one means for providing a reference signal that compensates for fluctuations in bloodstream temperature introduced by factors other than the energy source. That is, the reference signal compensates for background bloodstream temperature. The other sensor is introduced into the arterial side of the circulatory system anywhere it senses blood temperature as affected by the energy source. It may be introduced by a second catheter, for example an arterial catheter. Blood flow and/or cardiac output may then be calculated as described above.

In accordance with a further embodiment of the invention, a temperature sensor that also acts as a source of thermal energy, e.g., a thermistor, is positioned at a third location in the cardiac blood flow path. Power is supplied to the sensor sufficient to elevate the temperature of the sensor from a first temperature level to a second temperature level. In one embodiment of the invention, the temperature of the sensor is changed from the first to the second level and is maintained constant at said second level by varying the power that is supplied thereto. Such varying power is proportional to the instantaneous flow velocity and, hence, assuming a constant flow area, is proportional to the instantaneous cardiac output. Measurement of the sensor heating power and the temperature increment at the sensor can thus be used to continuously effect a determination of the instantaneous cardiac output. Further, for example, when the sensor is placed downstream at the outlet of one of the heart chambers, the variation in flow output over the cardiac cycle can be analyzed to provide an indication of the regurgitation characteristics of the heart outlet valve over the cardiac cycle. Moreover, such instantaneous cardiac output determination can be further refined to compensate for fluctuations in the temperature of the blood flowing through the heart by measuring the instantaneous temperature of the blood with another temperature sensor at a nearby location and appropriately taking into account such temperature variations when determining the cardiac output.

In another application, both the continuous cardiac output determinations and the instantaneous cardiac output determinations, as described above, can be combined. Thus, three temperature sensors and a source of thermal energy can all be used in combination to simultaneously provide an accurate and effectively continuous determination of time-averaged cardiac output, and a determination of instantaneous cardiac output at each instant of the cardiac cycle in still another application, two temperature sensors and a source of thermal energy can be used in an appropriate sequence to provide the averaged cardiac output determination and the instantaneous cardiac output determination.

BRIEF DESCRIPTION OF THE DRAWINGS

The invention is described in detail with the help of the accompanying drawings wherein:

FIGS. 8A, 8B and 8C show flow charts depicting modes of operating the process of the invention;

FIGS. 9A, 9B, and 9C show graphs of parameter relationships used in the invention; and FIG. 10 shows a graph useful for calibrating the flow values for a catheter used in the invention.

DESCRIPTION OF THE INVENTION

Figure 1:
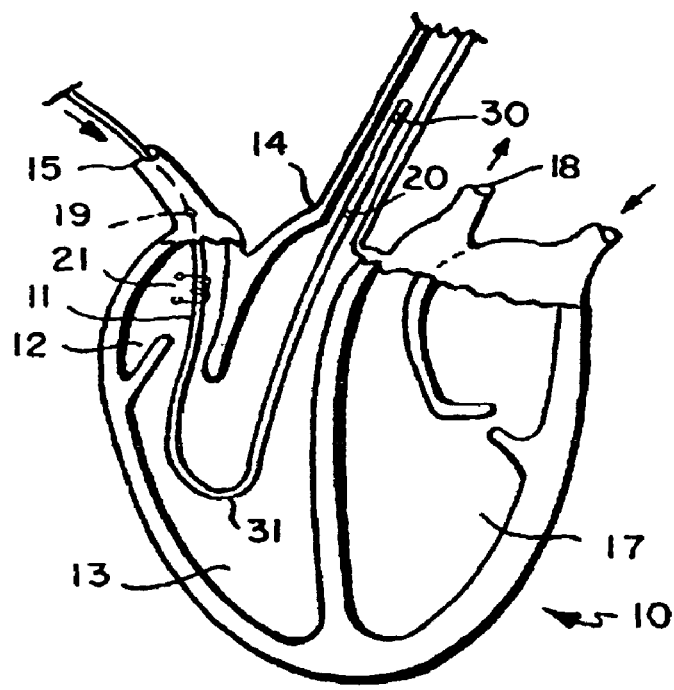
FIG. 1 shows a simplified diagrammatic view of a human heart.

As can be seen in FIG. 1, which represents a human heart 10 in a much simplified diagrammatic form, a flexible catheter 11 is inserted through the veins into the right atrium, or auricle, 12 of the heart and, thence, through the right ventricle 13 until the end of the catheter resides in or near the exit, or pulmonary, artery 14 which leads to the lungs. As is well known, blood flows (as represented by the arrows) from the input vein 15, i.e., the vena cava, into the right atrium and right ventricle and thence outwardly to the lungs and subsequently returns from the lungs into the left atrium 16, through the left ventricle 17 and thence outwardly into the aorta 18.

In accordance with the embodiment of the invention, shown with reference to FIG. 1, temperature sensors, e.g., thermistors, are carried by the catheter so that, when inserted as shown in FIG. 1, a first sensor 19 is positioned at a location within the vena cava 15 or right atrium 12 and a second sensor 20 is positioned at a location in or near the pulmonary artery 14.

Figure 2:
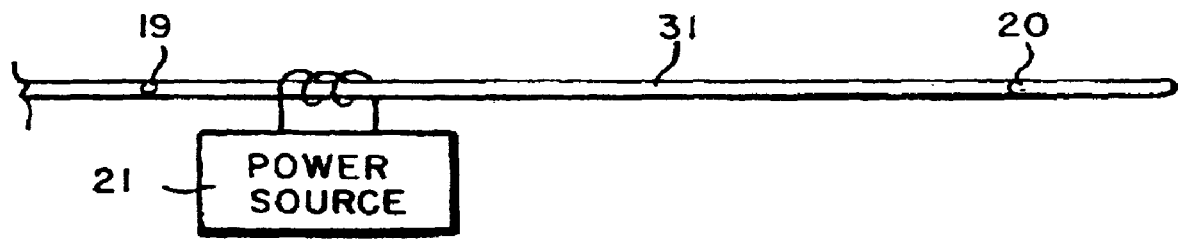
FIG. 2 shows a simplified diagrammatic view of a catheter useful in the invention.

For simplicity, the flexible catheter 11 is depicted in FIG. 2 in an extended condition with temperature sensors 19 and 20 at two different locations for measuring temperatures $T_1$ and $T_2$, respectively. A power source 21 of thermal energy which is borne, or carried, by the catheter 11 is positioned in the right atrium at a location between sensors 19 and 20. In a particular embodiment, the catheter-borne source is, for example, a coil of resistive wire placed on or embedded in the surface of catheter 11, to which an AC or a DC voltage (not shown) at a controllable level is supplied so as to generate thermal energy, i.e. heat. The magnitude of the thermal energy can be suitably controlled to insert a predetermined amount of thermal energy at a selected time, which thermal energy is transferred to the blood flowing through the heart so as to raise its temperature. The energy source is positioned at a sufficient distance from the sensor 19 that the latter is effectively thermally isolated from the site of the thermal energy source.

While the locations of the sensors 19 and 20 and the energy source 21 can be as shown in FIG. 1, alternative locations can also be used. Thus, the sensor 19 can be positioned in the vena cava 15, while the energy source 21 is located in the right atrium 12 and the sensor 20 in either the right atrium or the right ventricle. Moreover, if sensor 19 is positioned in the vena cava 15, the entire energy source 21, which is normally elongated, need not be located in the right atrium and can have a portion thereof in the vena cava and a portion thereof in the right atrium. Such source should preferably be at least partially located in the right atrium. Further, sensor 20 may be positioned in the right ventricle near the pulmonary artery 14 or may be located in the pulmonary artery itself at or near the right ventricle.

The temperatures $T_1$ and $T_2$ at locations 19 and 20 upstream and downstream, respectively, from the thermal energy source 21 are monitored and processed appropriately by a digital microprocessor. In accordance with the invention, the instantaneous temperatures are obtained as the outputs $T_1(t)$ and $T_2(t)$ of the temperature sensors 19 and 20, respectively. The outputs are connected to a differential amplifier to generate an analog signal which is proportional to the temperature difference $\Delta T(t)=T_1(t)-T_2(t)$ between them. The temperature difference signal $\Delta T(t)$ is digitized and sampled at selected time intervals by an analog-to-digital/sampling circuit. The digitized sampled temperature difference values and the known thermal energy values are supplied to a digital microprocessor which then suitably processes the data to provide the desired cardiac output information. The processing stages used in the host microprocessor are implemented by suitable programming of the microprocessor and are discussed below with the help of FIGS. 3-6.

The source 21 of thermal energy is alternately turned on and off. If it is assumed that thermal stability is reached after each change and that there is a substantially constant rate of blood flow, a stable temperature difference can be measured in each case. The quantity of blood flowing past the thermal energy source, i.e., the cardiac output, can be derived from such temperature difference measurements. However, such derivation is complicated by two factors which may affect the measurement of blood flow. First, the rate of blood flow through the heart is not substantially constant but surges with each heart contraction. Second, the temperature of the blood flowing through the heart is not constant but varies with each respiratory (breathing) cycle. In a preferred embodiment, the processing of the data takes such factors into account, as discussed below.

Figure 3:
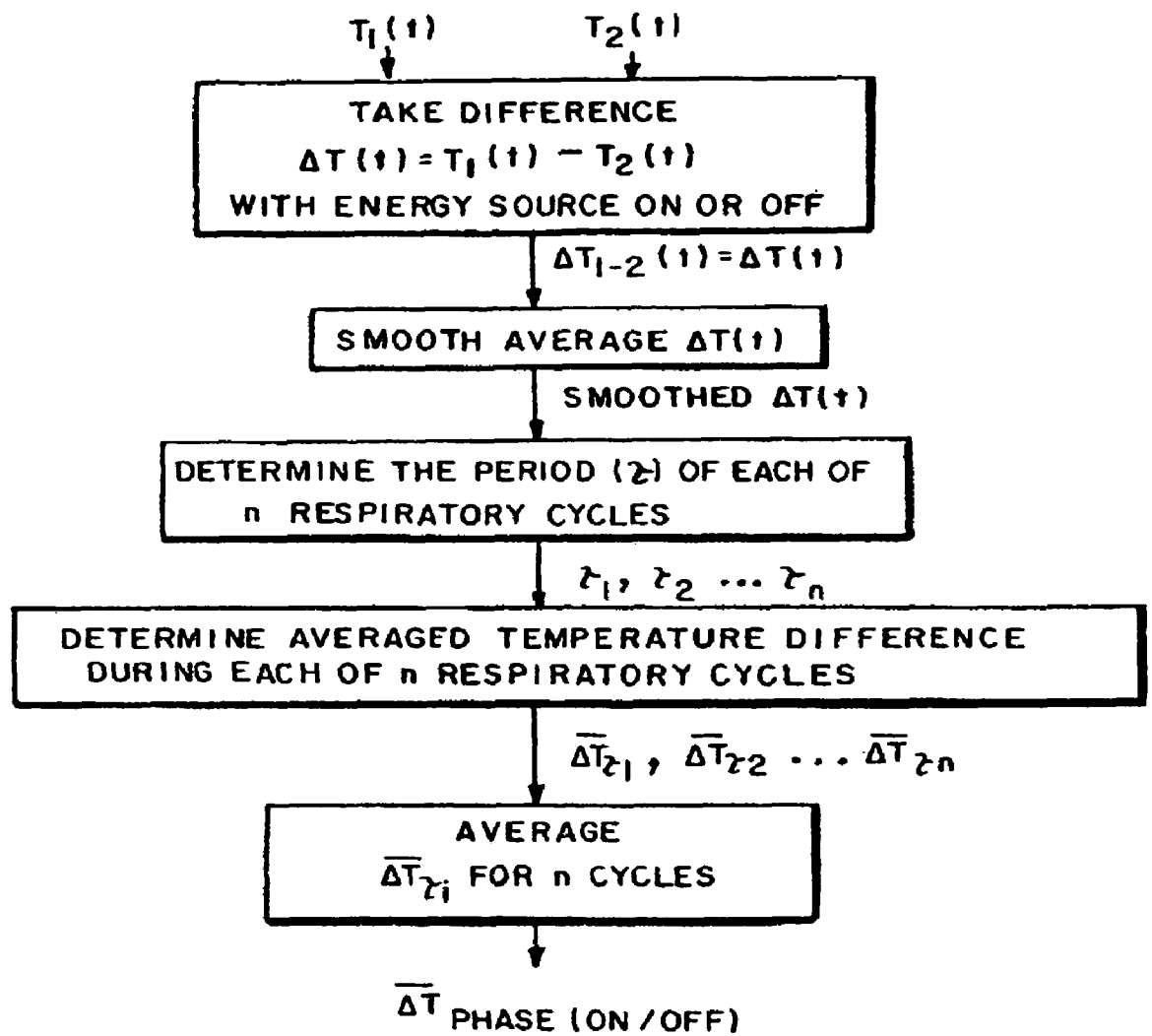
FIG. 3 shows a flow chart depicting steps in a process used in the invention.
Figure 4:
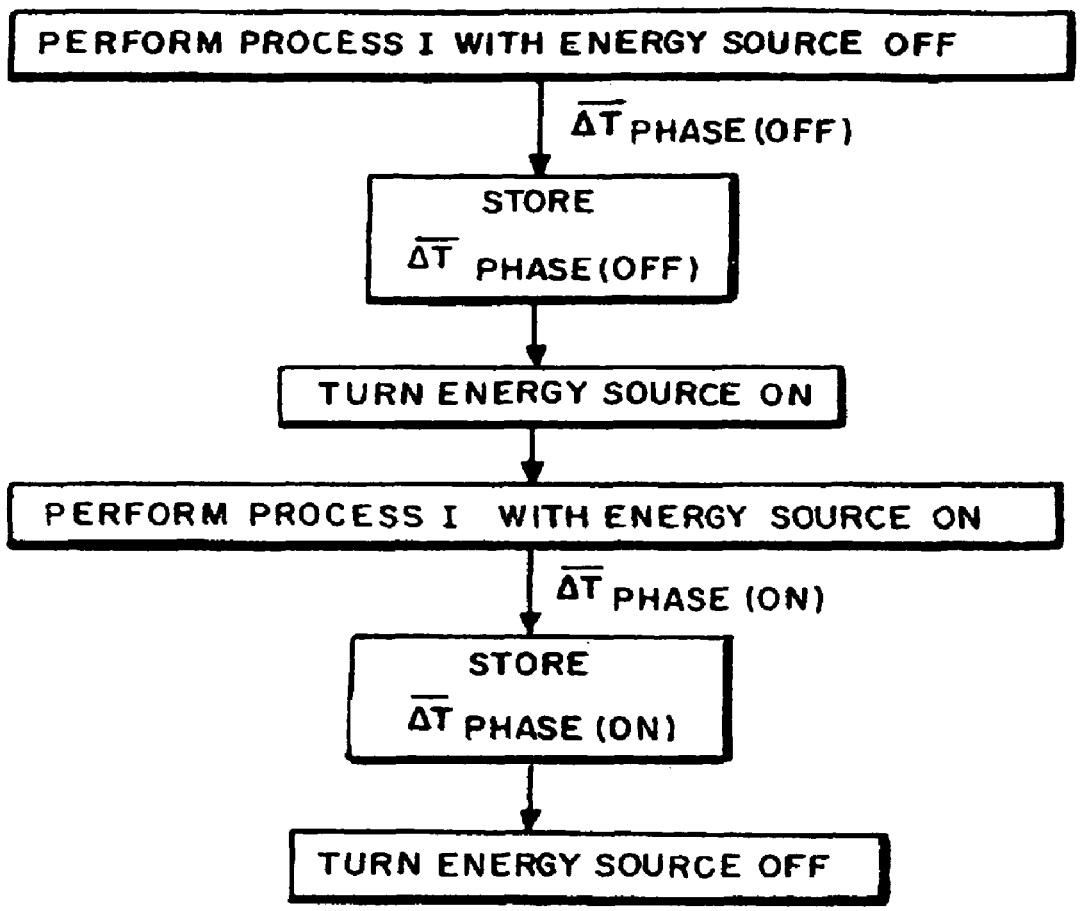
FIG. 4 shows a flow chart depicting further steps in a process used in the invention.
Figure 5:
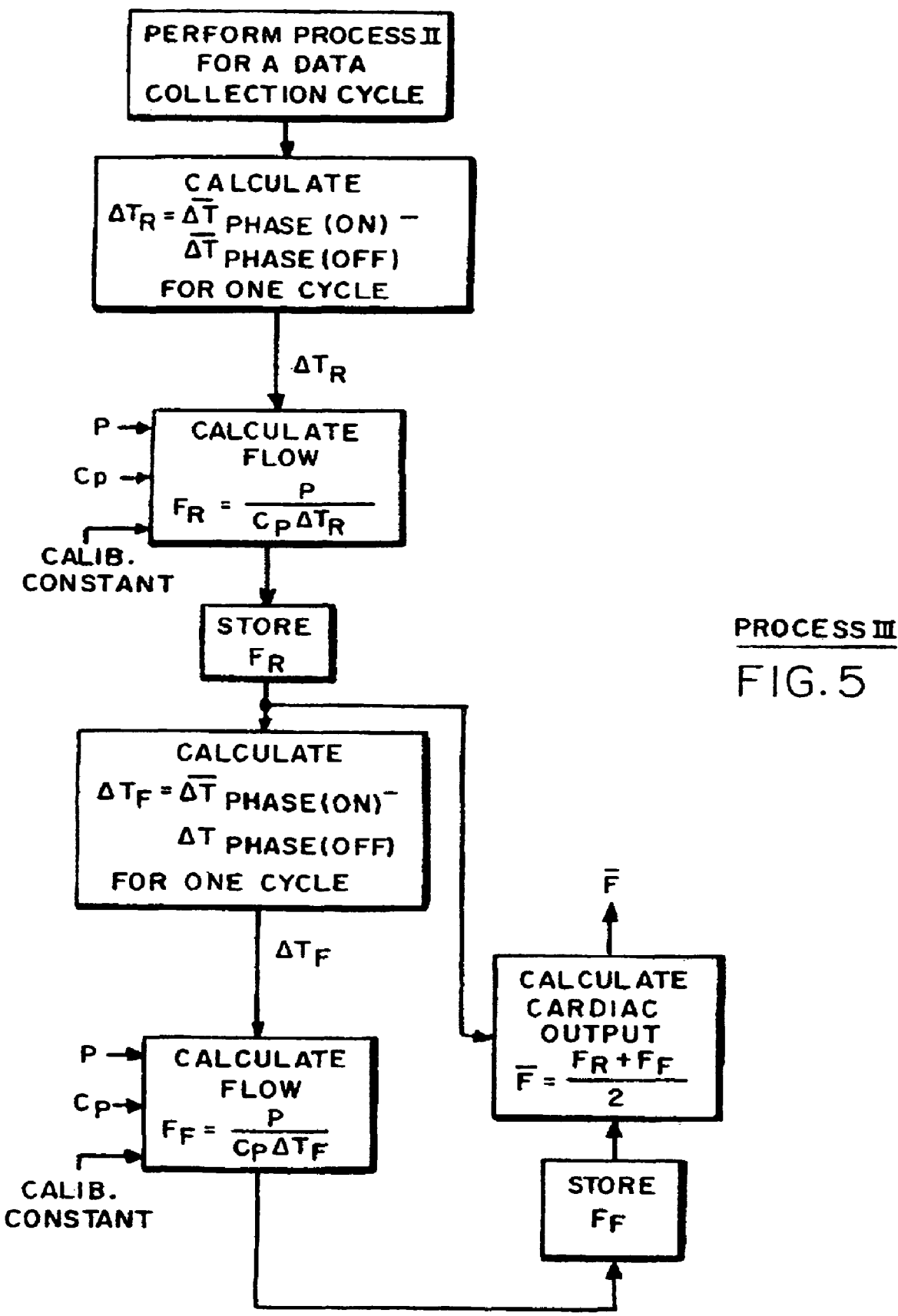
FIG. 5 shows a flow chart depicting still further steps in a process of the invention.

The process for determining cardiac output is performed in a microprocessor 2 which in a first embodiment is programmed to respond to the temperatures sensed at T.sub.1 and T.sub.2 and to perform the steps depicted in accordance with the flow charts shown in FIGS. 3-5. From a knowledge of such flow charts, it would be well within the skill of those in the art to appropriately program any suitable and known digital microprocessor, such as a personal computer, to perform the steps shown.

Figure 3A:
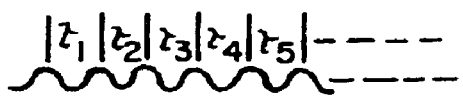
FIG. 3A shows a smooth temperature difference curve obtained in the process depicted in FIG. 3.

FIG. 3 depicts a basic process, identified as Process I, which is used in the overall processing of temperature data for determining cardiac output, as subsequently depicted in FIGS. 4 and 5. In the basic process shown in FIG. 3, a temperature difference as a function of time $\Delta T(t)$ is determined by a differential amplifier which responds to $T_1(t)$ and $T_2(t)$. Such differences may be effectively smoothed, or filtered, to produce a smooth temperature difference curve, as shown in FIG. 3A, which varies as a function of time in a cyclic manner which depends principally on the respiratory cycle of the person whose cardiac output is being determined.

The periods $\tau_1, \tau_2 \ldots \tau_n$ for each respiratory cycle are determined over n cycles. A characteristic of the temperature difference at each cycle is determined. For example, such characteristic preferably is the averaged temperature difference during each cycle ($\Delta T\tau_1, \Delta T\tau_2 \ldots \Delta T\tau_2 \ldots \Delta T\tau_n$).

(Alternatively, for example, the peak temperature differences may be the determined characteristic.) These averaged temperature differences ($\Delta T_{\tau n}$) are added for the n cycles involved and are divided by n to determine an averaged temperature difference per cycle ($\Delta T_{\tau n}$). The use of Process I is depicted in the process steps shown in FIG. 4, identified as Process II.

As seen therein, the steps of Process I are first performed when the source 21 of thermal energy (i.e., a heater) is turned off and the average $\overline{\Delta T}_{off}$ value per cycle is determined and suitably stored. The sampling time at which such determination is made is depicted in FIG. 6 as the sample time period S1.

Figure 6:
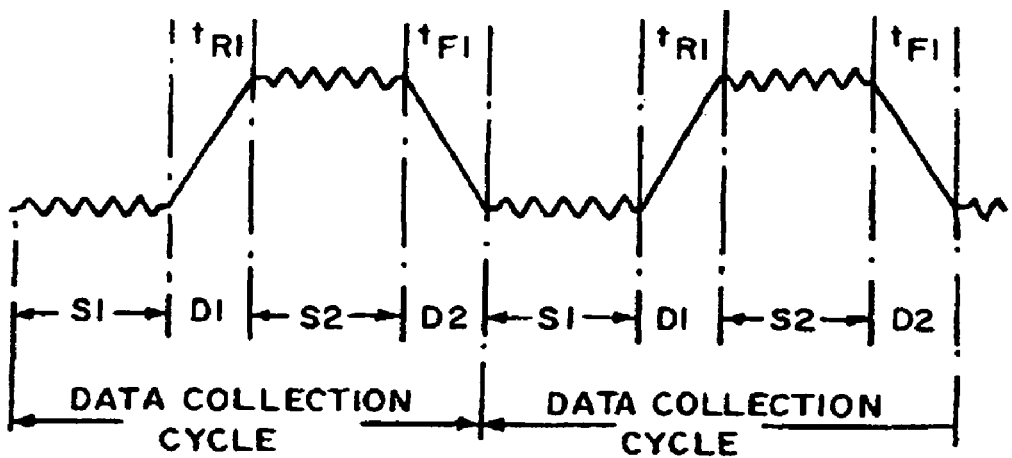
FIG. 6 shows a graph depicting a temperature/time relation used in the invention.

The heater 21 is then turned on for a specific time period to supply a known amount of power P to the blood flowing through the heart and, accordingly, the temperature of the blood flowing past the heater rises and the temperature difference $\Delta T(t)$ rises over a transition, or delay, rise time period, $t_{R1}$, shown in FIG. 6 and designated as D1, after which the temperature difference generally stabilizes over a second sample time period S2. As seen in FIG. 4, after the heater 21 is turned on and the temperature has stabilized, Process I is performed, again over n cycles, e.g., over the time period S2, and the averaged temperature difference $\Delta T_{on}$ is determined with the heater turned on and is suitably stored. The heater is then turned off and the temperature falls over a transition, or delay, fall time period t.sub.F1, shown in FIG. 6 and designated as D2, generally to its former value.

Cardiac output is calculated using the averaged temperature differences when the energy is off and the averaged temperature differences when the energy is on, by the relationship:

$$F = \frac{P}{C_p(\overline{\Delta T}_{on} - \overline{\Delta T}_{off})}$$

where:
F=Flow
P=Power
$C_P$=heat capacitance
$\overline{\Delta T}_{on}$=average temperature for power on
$\overline{\Delta T}_{off}$=average temperature for power off.

As seen in FIG. 5, the steps of Process II are repeated indefinitely for N data collection cycles, a data collection cycle being designated as including the time periods S1, D1, S2, and D2, as shown in FIG. 6. For each data collection cycle the rise time temperature difference $\Delta TR$ between the averaged temperature difference $\overline{\Delta T}_{on}$ at S2 and the averaged temperature difference $\overline{\Delta T}_{off}$ at S1 and the fall time temperature difference $\Delta T_F$ between the averaged temperature difference $\overline{\Delta T}_{off}$ at S1 and the averaged temperature difference $\overline{\Delta T}_{on}$ at S2 are determined.

The flow, $F_R$, is calculated for each data collection cycle from the known amount of power P introduced into the blood flow stream by the energy source, or heater 21, from the known heat capacitance of blood, $C_P$, and from the difference in the averaged temperature differences $\overline{\Delta T}_{on}$ and $\overline{\Delta T}_{off}$, which occurs over the data collection cycle S1+D1+S2 in accordance with the following relationship:

$$F_R = \frac{P}{C_p(\overline{\Delta T}_{on} - \overline{\Delta T}_{off})}$$

In a similar manner, the flow $F_F$ is calculated from P, $C_P$ and the difference in the averaged temperature differences $\Delta T_{on}$ and $\Delta T_{off}$ which occurs over the later portion of the data collection cycle S1+D1+S2 in accordance with the following relationship:

$$F_F = \frac{P}{C_p(\overline{\Delta T}_{on} - \overline{\Delta T}_{off})}$$

$F_R$ and $F_F$ can be averaged to obtain the averaged flow ($\overline{F}$) over one data collection cycle as shown in FIG. 6.

$$\overline{F} = \frac{F_R + F_F}{2}$$

A suitable calibration constant can be used to adjust the values of $F_R$, $F_F$ and $\overline{F}$.

Accordingly, by using two temperature sensors 19 and 20, cardiac output can be determined several times a minute in accordance with FIGS. 3-6, yielding an effectively continuous cardiac output value. Because such measurements can be made using relatively low power levels, the danger that the heart may be damaged by the introduction of thermal energy is substantially eliminated.

It will be apparent that the foregoing technique, which has been described in connection with the direct introduction of heat as an indicator agent and the measurement of temperature, can readily be performed by those skilled in the art by using indicator agents which affect the pH of the blood or change other blood parameters.

Figure 11:
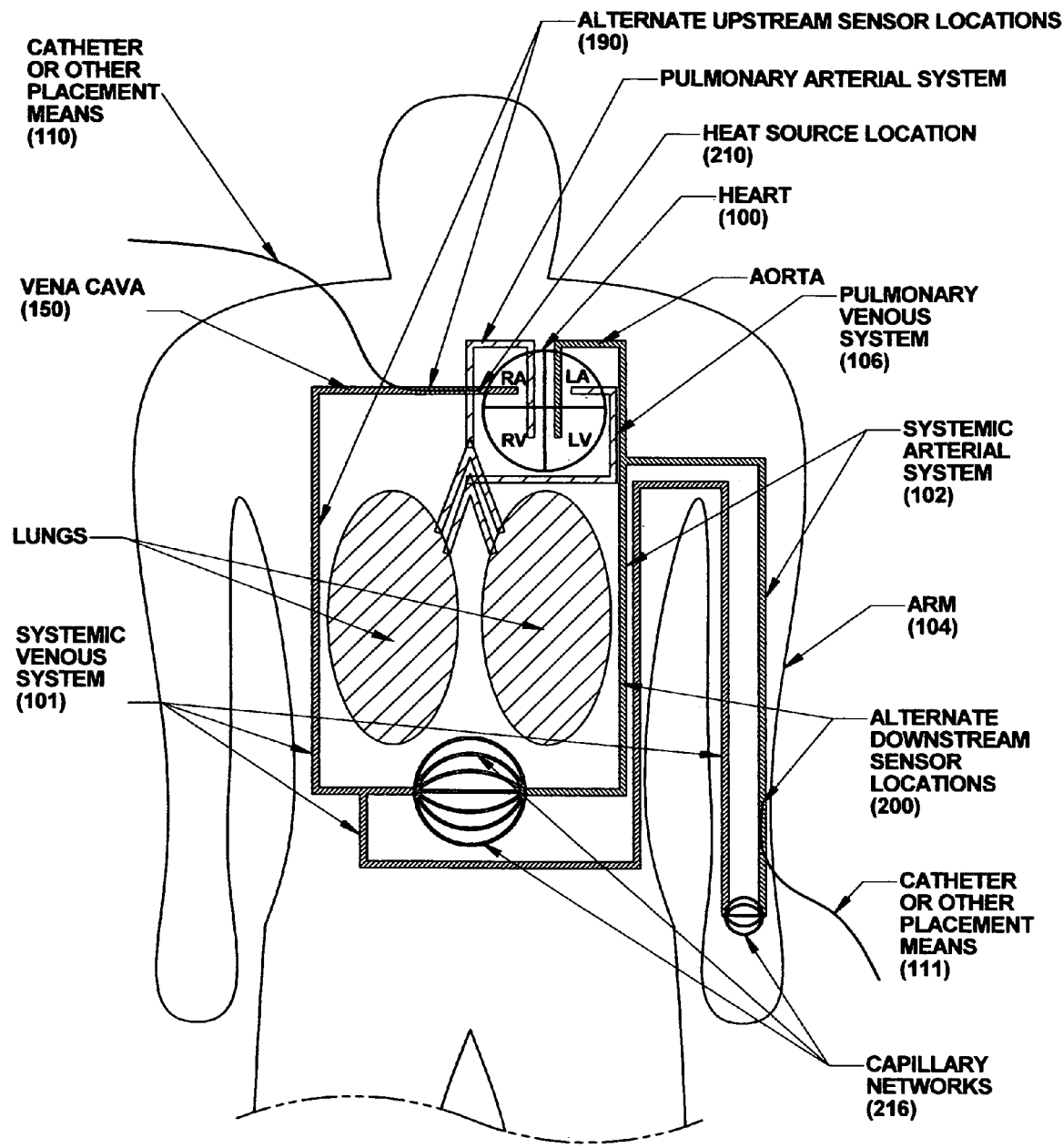
FIG. 11 is a diagram of another catheter configuration.

The system can be located in the body of a subject as illustrated in the diagrammatic representation of the circulatory system shown in FIG. 11. The circulatory system illustrated there includes systemic venous system 101, vena cava 150, heart 100, systemic arterial system 102, pulmonary venous system 106 and the body's capillary system 216. The representation of the capillary system 216 is intended to indicate that system anywhere in the body. The representation of the heart 100 includes the right atrium (RA), the right ventricle (RV), the left atrium (LA) and the left ventricle (LV).

An energy source 210 and a sensor 190 are located in the venous side 101 of the circulatory system of the subject by any suitable placement method or means. For example, a catheter 110 may be introduced into the vena cava 150 to locate the energy source 210 in or near the vena cava or within the heart 100 and the sensor 190 somewhere in the venous system upstream of the energy source 210.

FIG. 11 shows the energy source 210 in the vena cava 150 while FIG. 1 shows an energy source 21 in the right atrium 12. The energy sources 21 and 210 are similar in function and may be similar in construction. Sensor 190 is located upstream of the energy source 210 where it is not materially affected by output from the energy source, where it senses blood temperature unaffected by the energy source. Sensor 190 or other suitable reference provides a reference signal that compensates for temperature level and fluctuations in bloodstream introduced by factors other than the energy source 210. That is, the reference signal corresponds to background bloodstream temperature, unperturbed by the energy source 210. FIG. 11 shows one preferred location for sensor 190 in or near the vena cava and an alternate location more remote from the energy source. In another embodiment of the system a fixed resistor or other reference value that approximates the unperturbed blood temperature could be used, in lieu of the value provided by the sensor 190, to compensate for background bloodstream temperature. (This likely would reduce the accuracy of the compensation and its use would depend on the requirements of the user.) Sensor 190 can be similar in construction and is similar in function to sensor 19 shown in FIG. 1.

The sensor 200 is located in the arterial system 102 and may be introduced by any suitable method or means. For example, an arterial catheter may be used. The sensor 200 may be located anywhere on the arterial side 102 of the body where it senses blood temperature affected by the energy source 210. The sensor 200 can be located, for example, in the arm 104, leg or neck. The sensor 200 and the sensor 20 shown in FIG. 1 can be similar in construction and are similar in function.

When the system is configured as shown in FIG. 11, cardiac output and blood flow may be calculated as previously described. When the sensor 200 and the energy source 210 are separated by such a distance that a material amount of thermal energy from the energy source is lost to the body before reaching sensor 200, a compensating factor is included in the calibration constant referenced in FIG. 5.

Figure 7A:
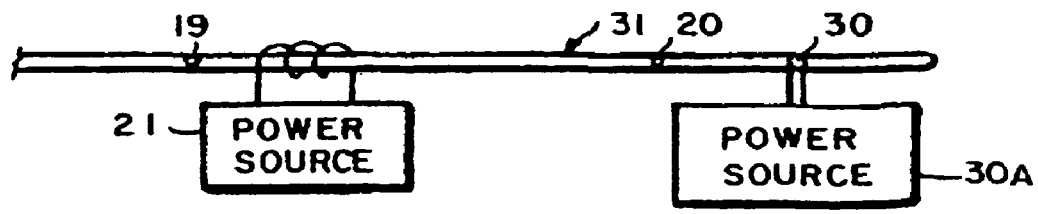
FIG. 7A shows a simplified diagrammatic view of another catheter used in the invention.
Figure 7B:
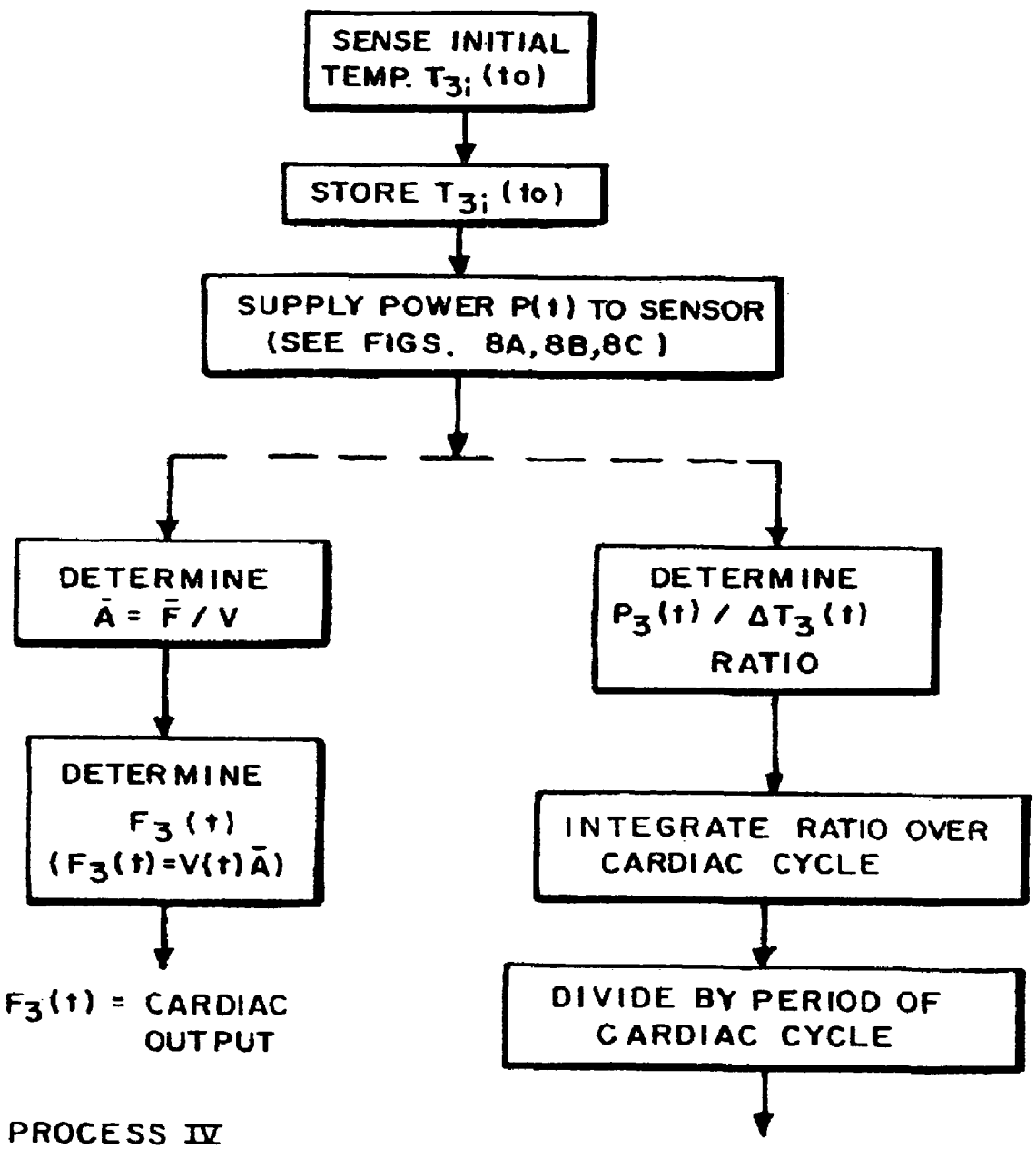
FIG. 7B shows a flow chart depicting steps in still another process of the invention.

In some situations it may be desirable to provide more frequent indications of cardiac output, such as, for example, the instantaneous cardiac output or the cardiac output averaged over each individual cardiac cycle (i.e. each heart beat). Such information can be provided using the further embodiments of the invention discussed below with reference to FIGS. 7-8. A single temperature sensor 30 at a location near the distal end of the catheter 31 (as shown in FIG. 7A) can be used to determine the instantaneous or beat-to-beat blood velocity V(t). The blood velocity can be combined with the cardiac output averaged over one or more data collection cycles to calculate instantaneous cardiac output. The process used is shown in the process depicted in FIG. 7B, identified as Process IV.

As seen therein, the initial temperature $T_{3i}(t)$ sensed at temperature sensor 30 as a function of time is smoothed, or filtered, in the manner as previously discussed above, and suitably measured and stored at an initial time $t_o$. A predetermined rise in temperature $\Delta T_3$ of the temperature sensor itself is selected. Power is then supplied at time $t_o$ to the temperature sensor 30 from a power source 30A connected thereto to cause its temperature $T_3(t)$ to rise by a predetermined amount.

Power may be supplied to the sensor in different ways according to the needs of the particular measurement and the relative simplicity or complexity of the required circuitry, three such ways being depicted in FIGS. 8A, 8B, and 8C.

For example, in a first mode of operation (FIG. 8A), heating power may be supplied to the sensor in such a manner as to keep the final sensor temperature $T_{3f}(t)$ constant at an initial level $\Delta T_3$ above the initial temperature $T_{3i}(t_o)$, i.e. $T_{3f}=T_{3i}(t_o)+\Delta T_3$ even when the local blood temperature varies with time, as illustrated in FIG. 9A. Under such conditions, the sensor is maintained at a time-varying temperature increment $\Delta T_3(t)$ above the instantaneous local blood temperature, $T_b(t)$.

Alternatively, in a second mode of operation, power can be supplied to the sensor so as to continuously maintain the sensor at a fixed temperature increment above the time varying local blood temperature, as illustrated in FIG. 9B. Under such conditions, $\Delta T_3(t)=\Delta T_3$, a constant, and the sensor temperature varies according to $T_{3f}(t)=\Delta T_3+\Delta T_{3i}(t)$.

A third mode of heating may also be convenient when the temperature sensors are temperature-sensitive resistors, or thermistors. Thus, when a thermistor is used, it may be more convenient to design an electrical heating circuit that maintains the sensor at a constant resistance increment above the resistance of the sensor that corresponds to the local blood temperature. If R is the corresponding resistance for a sensor temperature T, then these conditions are represented by $\Delta R_3(t)=\Delta R_3$, a constant, and the sensor resistance varies according to $R_{3f}(t)=\Delta R_3+\Delta R_{3i}(t)$, as illustrated in FIG. 9C. The change in temperature $\Delta T_3(t)$ is then replaced by the change in resistance $R_3(t)$ in the ratio which is integrated over a cardiac cycle. Further details and exemplary apparatus for such modes of operation are presented and described in U.S. Pat. No. 4,059,982, issued to E. F. Bowman on Nov. 29, 1977. With all three of the above approaches, power (P) is supplied to produce a temperature rise ($\Delta T$) both of which are then related to the instantaneous blood velocity and, hence, blood flow.

Techniques in which sensor heating power and temperature can be measured and used to provide more detailed information on cardiac output are described below. The technique involved can be applied to measure both instantaneous cardiac output, and the cardiac output for an individual cardiac cycle. Such detailed measurement information greatly enhances the diagnostic capability of a physician.

First, a method is described to measure instantaneous volumetric flow (which flow if measured at the location described above is the cardiac output). For each of the particular implementations described above, the power $P_3(t)$ applied to the temperature sensor 30 is controlled so as to maintain the final temperature of the sensor at a desired value $T_{3f}$. The power applied to the temperature sensor 30 or, more generally, the ratio of the power applied to the sensor to the temperature increment, $P_3(t)/\Delta T_3(t)$, is directly correlated with the fluid and flow properties of the flowing liquid about the sensor.

For example, the relationship between required sensor power and local fluid velocity, V(t), is given by a correlation of the form:

$$P(t)=4\pi ka\Delta T(t)[1+C_1 P_r^n (2a\rho V(t)/\mu)^m]$$

Where
  P(t)=instantaneous power to sensor
  k=thermal conductivity of fluid
  a=sensor radius
  $\Delta T(t)$=instantaneous temperature difference between heated sensor and unheated fluid temperature.
  $C_1$=constant of calibration
  $P_r$=a nondimensional "Prandtl" number which relates to the viscosity $\mu$, heat capacity
  Cp and thermal conductivity k of a fluid.
  n,m=power factors which are determined from experimental data
  $\rho$=fluid density
  $\mu$=viscosity
  V(t)=instantaneous fluid velocity The fluid flow velocity in the vicinity of the sensor can be determined from the required sensor heating power. Volumetric flow in the vessel can then be determined with one further assumption for the distribution of the fluid flow within the vessel. For example, assuming a uniform velocity profile within the vessel, volumetric flow $F_3$ is given by $$F_3=VA$$

where V is the fluid velocity in the vessel and A is the flow area.

If the fluid flow area A is not previously known, it may be inferred from the measurement of average volumetric flow in the vessel. Such average volumetric flow can be determined, for example, by using the techniques of the invention already described above herein or by using other techniques for yielding comparable information. For example, if F is the average cardiac output, typically measured over several cardiac cycles, as described above, and V is the average fluid velocity, determined by calculating an average value for the instantaneous flow velocity over at least one cardiac cycle, then one such estimate for the average flow area A is given by $$\overline{A}=\overline{F}/\overline{V}$$

Therefore, given the sensor measured heating power, first the fluid velocity and then volumetric flow can be calculated at any desired instant in time, i.e., $F_{3(t)}=V(E)\overline{A}$, yielding an instantaneous measure of volumetric flow, i.e., cardiac output.

In another embodiment, a method to measure cardiac output over a single cardiac cycle is described. As described above in different implementations, the power $P_3(t)$ applied to the temperature sensor 30 is controlled so as to maintain the temperature of the sensor at a desired signal value $T_{3f}$. The power applied to the temperature sensor 30, or more generally, as discussed above, the ratio of the power applied to the sensor to the temperature increment, i.e., $P_3(t)/\Delta T_3(t)$, is directly correlated with the properties of the fluid flow in the vicinity of the sensor.

Thus, the integrated value of the power to temperature ratio over a single cardiac cycle is directly correlated with, i.e., is proportional to the average cardiac output over the cardiac cycle, $$\int_{cardiac \cdot cycle} \frac{P_3(t)}{\Delta T_3(t)} dt \propto \overline{F}$$

or, alternatively expressed $$\frac{1}{T}\int_{cardiac \cdot cycle} \frac{P_3(t)}{\Delta T_3(t)} dt \propto \overline{F}$$

where T represents the period of the cardiac cycle and F correspondingly represents cardiac output averaged over the cardiac cycle. Thus, the average cardiac output F over an individual cardiac cycle then can be determined from the measured and integrated power and temperature signals from the sensor.

Furthermore, an explicit correlation for integrated power and average cardiac output over the cardiac cycle may be dispensed with if a simple qualitative indication of the change in cardiac output on a cardiac cycle-to-cardiac cycle basis is desired. To obtain such information, a given measurement of cardiac output is taken as associated with a corresponding measured value of the integrated sensor signal over a cardiac cycle. The measurement of cardiac output could be obtained intermittently by the techniques described in this invention or other similar techniques. Since cardiac output is known to be correlated with the value of the integrated sensor signal over the cardiac cycle, any changes in the sensor signal indicate a corresponding change in cardiac output.

In certain situations, it may be desirable to compensate for temperature variations in the blood which is flowing past the sensor, as this may affect the value of F(t). A process for such compensation is depicted as Process IV in FIG. 7B wherein a temperature $T_2(t)$ is sensed by a second sensor (which may be, for example, sensor 19 or sensor 20) at a location remote from sensor 30 (see FIG. 7A). For example, knowledge of the instantaneous blood temperature is required for the process in which the heated sensor is maintained at a constant increment above the local blood temperature. In this case, the temperature $T_2(t)$ is used as a proxy for the temperature $T_3(t)$ which would be measured in the absence of sensor heating.

In a further alternative embodiment, where only two sensors 19 and 20 are utilized (as shown in FIG. 2), sensor 20 can be used as the primary sensor when calculating instantaneous cardiac output (equivalent to sensor 30 in FIG. 7A) and sensor 19 can be used as the secondary temperature compensation sensor. In such an embodiment, the averaged cardiac output can be determined using sensors 19 and 20, as set forth in FIGS. 3-6 and the instantaneous cardiac output can then subsequently be determined using sensors 19 and 20, as set forth in FIG. 7B and either FIG. 8A, 8B or 8C, such average and instantaneous cardiac output determinations being made in sequence by the microprocessor to provide the cardiac information in both forms, as desired.

As mentioned above, when using the above described catheter, the various flow values which are determined in accordance with the processes as discussed above are proportional to flow but may not be equal to the actual flow values unless they are suitably calibrated since the correspondence between the calculated and actual values depends on the manner in which a particular catheter is constructed and used. A calibration constant for a particular catheter can be represented by the slope and intercept of a curve which relates the calculated flow and the actual flow, in accordance with the following relationship:

$$F_{actual} = aF_{calc.} + b$$

where, as illustrated in FIG. 10, "a" is the slope of a straight line 35 and "b" is the intercept thereof along the vertical axis. Curve 35 can be obtained by using a known catheter and known flow values therein to construct a curve 36. The best straight line fit is determined as line 35. The slope "a" and intercept "b" are thereby determined. Such determined values for "a" and "b" can be used with the calculated flow values in each case to determine the actual flow from the calculated flow. While the above description discusses preferred embodiments of the invention, modifications thereof may occur to those in the art within the spirit and scope of the invention. Hence, the invention is not to be construed as limited to particular embodiments described, except as defined by the appended claims.

The invention claimed is:

1. A system for quantifying blood flow in a living subject comprising:
    (a) a thermal energy source for increasing blood temperature at a location in the venous side of the circulatory system during preselected time intervals;
    (b) a first sensor for sensing blood temperature in the venous side of the circulatory system where blood temperature is substantially unaffected by the output of the thermal energy source;
    (c) a second sensor for sensing blood temperature in the arterial blood flow path where the blood temperature is affected by the output of the thermal energy source; and
    (d) means responsive to the first and second sensors and output of said thermal energy source for calculating a blood flow related value as a function of outputs of the first and second sensors when blood temperature in the arterial side of the circulatory system is affected by output of said thermal energy source and the outputs of the first and second sensors when blood temperature in the arterial side of the circulatory system is not substantially affected by said thermal energy source.

2. A system according to claim 1 further comprising a catheter adapted to be introduced into the venous system for supporting one or both of the first sensor and the thermal energy source.

3. A system for quantifying blood flow in a living subject comprising:
    (a) a thermal energy source for increasing blood temperature at a location in the venous side of the circulatory system during preselected time intervals;
    (b) a first sensor for sensing blood temperature in the venous side of the circulatory system where blood temperature is substantially unaffected by the output of the thermal energy source;
    (c) a second sensor for sensing blood temperature in the arterial blood flow path where the blood temperature is affected by the output of the thermal energy source; and
    (d) means for calculating blood flow as a function of the output of the thermal energy source and the difference between
        the temperature difference sensed by the first and second sensors when the blood temperature in the arterial side of the circulatory system is affected by output of the thermal energy source and
        the temperature difference sensed by the first and second sensors when the thermal energy source is not activated.

4. A system according to claim 1 wherein the thermal energy source comprises an energy source for increasing blood temperature in or near the right atrium or vena cava and said calculating means calculates a blood flow value that corresponds to cardiac output.

5. A system for quantifying blood flow in the circulatory system of a living subject comprising:
    (a) heating means adapted to be located in the venous flow path for intermittently elevating the temperature of blood in the arterial flow path;
    (b) means for sensing blood temperature in the arterial flow path;
    (c) means for providing a value corresponding to blood temperature at a location in the venous flow path not affected by the output of said heating means; and
    (d) means for calculating blood flow as a function of the output of said heating means when elevating blood temperature, the difference in the values from said sensing means and said providing means when the temperature of blood is not elevated by said heating means and the difference in the values from said sensing means and said providing means when the temperature of blood is elevated by said heating means.

6. A system according to claim 5 wherein said providing means comprises a second means for sensing blood temperature.

7. A method for calculating blood flow in the blood flow path of a living subject comprising:

(a) changing a thermal energy characteristic of blood at a site in the venous side of the circulatory system in or near the right atrium or vena cava during preselected time intervals;
(b) detecting the temperature difference between a location in the venous system substantially unaffected by said changes introduced at the site and a selected location in the arterial system where blood temperature is affected by said changing step;
(c) detecting the temperature difference between the location in the venous system and the location in the arterial system in the absence of said changing step; and
(d) calculating blood flow using a computer as a function of the temperature difference of the first said detecting step, the temperature difference of the second said detecting step and the change introduced by said changing step.

* * * * *